(12) United States Patent
Gayet et al.

(10) Patent No.: US 8,404,085 B2
(45) Date of Patent: Mar. 26, 2013

(54) SEPARATION AND PURIFICATION OF HYDROQUINONE FROM CRUDE MIXTURES THEREOF

(75) Inventors: Hubert Gayet, Villeurbanne (FR); Bruno Heinisch, Villeurbanne (FR)

(73) Assignee: Rhodia Operations, Aubervilliers (FR)

( * ) Notice: Subject to any disclaimer, the term of this patent is extended or adjusted under 35 U.S.C. 154(b) by 798 days.

(21) Appl. No.: 12/306,767

(22) PCT Filed: Jun. 27, 2007

(86) PCT No.: PCT/FR2007/001078
§ 371 (c)(1),
(2), (4) Date: Nov. 18, 2009

(87) PCT Pub. No.: WO2008/000954
PCT Pub. Date: Jan. 3, 2008

(65) Prior Publication Data
US 2010/0059359 A1   Mar. 11, 2010

(30) Foreign Application Priority Data
Jun. 29, 2006 (FR) ..................... 06 05870

(51) Int. Cl.
*B01D 3/14* (2006.01)
*B01D 3/42* (2006.01)
*C07C 37/74* (2006.01)

(52) U.S. Cl. ............... 203/1; 203/3; 203/71; 203/80; 568/752; 568/753; 202/154; 202/173

(58) Field of Classification Search ............ 203/1, 3, 203/71, 80, 99, DIG. 19; 568/752, 753; 202/154, 202/158, 172, 173
See application file for complete search history.

(56) References Cited

U.S. PATENT DOCUMENTS 4,308,110 A * 12/1981 Hosaka et al. ............... 203/48
6,844,472 B1 * 1/2005 Bourdon et al. ............. 568/758
8,071,817 B2 * 12/2011 Gayet et al. ................. 568/753

FOREIGN PATENT DOCUMENTS
FR   2788763 A1   7/2000

OTHER PUBLICATIONS
International Search Report corresponding to PCT/FR 2007/001078.

* cited by examiner

*Primary Examiner* — Virginia Manoharan
(74) *Attorney, Agent, or Firm* — SNR Denton US LLP

(57) ABSTRACT

Separation and purification of hydroquinone from crude mixtures thereof essentially containing hydroquinone in combination with very small amounts of impurities including resorcinol and pyrogallol, include a topping distillation allowing the resorcinol to be removed as the distillation top product, and allowing a crude mixture essentially containing hydroquinone and the heavy impurities to be recovered at the column bottom, such mixture then being subjected to a bottoming distillation which allows the pyrogallol to be removed at the column bottom and allows hydroquinone in a purified form to be recovered at the column top.

20 Claims, 2 Drawing Sheets

SEPARATION AND PURIFICATION OF HYDROQUINONE FROM CRUDE MIXTURES THEREOF

CROSS-REFERENCE TO EARLIER APPLICATIONS

This application is a national phase of PCT/FR 2007/001078, filed Jun. 27, 2007 designating the United States (published in the French language on Jan. 3, 2008, as WO 2008/000954 A2; the title and abstract were also published in English), which claims foreign priority under 35 U.S.C. §119 of FR 0605870, filed Jun. 29, 2006, each hereby expressly incorporated by reference in its entirety and each assigned to the assignee hereof.

The present invention relates to a separation and purification process which makes it possible to obtain purified hydroquinone from crude mixtures essentially comprising hydroquinone in combination with very small amounts of impurities, typically present in a proportion of 0.5 to 4% by weight.

The invention also relates to devices and in particular plants of industrial size which make possible the implementation of this process.

Hydroquinone (or 1,4-dihydroxybenzene) is a well known compound resulting from the phenol industry, where it is generally obtained as a mixture with various other dihydroxylated or trihydroxylated benzene compounds, such as pyrocatechol (1,2-dihydroxybenzene), resorcinol (1,3-dihydroxybenzene) or pyrogallol (1,2,3-trihydroxy-benzene).

One of the synthetic routes to hydroquinone consists in hydroxylating phenol with hydrogen peroxide, in particular in the presence of homogeneous or heterogeneous acid catalysts.

Thus, recourse may be had, as according to FR 2 071 464, to a strong protic acid, that is to say an acid exhibiting a pKa in water of less than 0.1, preferably of less than −1.

Mention may be made, as example of strong protic acids, inter alia, of sulfuric acid, chlorosulfuric acid, perchloric acid or sulfonic acids, such as, for example, methanesulfonic, trifluoromethanesulfonic, toluenesulfonic or phenolsulfonic acid.

Mention may be made, as other examples of protic acid catalysts, of sulfonic resins and more particularly the resins sold under various trade names. Mention may be made, inter alia, of the following resins: Temex 50, Amberlyst 15, Amberlyst 35, Amberlyst 36 and Dowex 50W.

The abovementioned resins are composed of a polystyrene backbone which carries functional groups which are sulfonic groups. The polystyrene backbone is obtained by polymerization of styrene and divinylbenzene, under the influence of an activation catalyst, generally an organic peroxide, which results in a crosslinked polystyrene which is subsequently treated with concentrated sulfuric acid or hydrochloric/sulfuric acid, resulting in a sulfonated styrene/divinylbenzene copolymer.

It is also possible to resort to sulfonic resins which are phenol/formaldehyde copolymers and which carry a methylenesulfonic group on the aromatic ring, for example the resin sold under the name Duolite Arc 9359.

Other commercially available resins are also suitable and mention may be made of perfluorinated resins carrying sulfonic groups and more particularly Nafion which is a copolymer of tetrafluoroethylene and of perfluoro[2-(fluorosulfonylethoxy)propyl]vinyl ether.

Mention may be made, as other catalysts suitable in hydroxylation processes, of iron(II) and copper(II) complexes (FR 2 121 000, USSR 1 502 559) and any other catalyst of Fenton type.

Other processes for the preparation of hydroquinone involve heterogeneous catalysis. Thus, use may be made of an acid zeolite of titanium silicalite (or titanosilicalite-1) type or of iron silicalite type of TS-1 type (FR 2 489 816), a zeolite of titanium silicalite MEL type (EP 1 131 264) or a titanozeosilite of MFI type (EP 1 123 159). It is also possible to use an MCM-22 zeolite (FR 2 856 681).

On conclusion of such hydroxylation reactions, a mixture is obtained which essentially comprises pyrocatechol and hydroquinone, in variable proportions with in general a pyrocatechol/hydroquinone ratio by weight of the order of 0.25 to 4.0, and also various by-products in much smaller amounts, in particular resorcinol and pyrogallol, generally at contents of 0.5 to 4.0% by weight, percentages expressed with respect to the amount of hydroquinone and pyrocatechol formed.

Mixtures of variable compositions are obtained which comprise, by weight, from 20 to 80% of pyrocatechol, from 80 to 20% of hydroquinone, from 0.1 to 2% of resorcinol and from 0.1 to 2% of pyrogallol.

Typically, mixtures are obtained which comprise, by weight, from 50 to 80% of pyrocatechol, from 20 to 50% of hydroquinone, from 0.1 to 2% of resorcinol and from 0.1 to 2% of pyrogallol.

In order to isolate the hydroquinone from crude mixtures of this type, one method currently known consists in distilling said mixture, making it possible to obtain, as distillation top product, pyrocatechol (which is the most volatile compound in the mixture) and, as distillation bottom product, a "crude hydroquinone", namely a mixture essentially comprising hydroquinone, in combination with small amounts of impurities (in particular resorcinol and pyrogallol, and also possible traces of pyrocatechol not removed by the distillation).

The problem at the basis of the invention is thus that of providing an economic process which makes possible the purification of a crude hydroquinone of the abovementioned type, namely essentially comprising hydroquinone in combination with very small amounts of impurities which have different natures, including resorcinol and pyrogallol.

The purification of hydroquinone presents several problems to a person skilled in the art.

Hydroquinone is a compound which exhibits a very high boiling point of greater than 200° C., even under a reduced pressure of 100 mbar.

Furthermore, hydroquinone is sensitive to thermal decomposition and results in colored decomposition products.

In the crude hydroquinone to be purified according to the invention, essentially hydroquinone is present, that is to say at least 90% by weight of hydroquinone is present, the remainder being composed of the impurities to be removed. Preferably, the crude hydroquinone comprises at least 96% by weight of hydroquinone.

In point of fact, there is great difficulty in removing extremely low contents of impurities.

Furthermore, the difficulty is increased due to the nature of the impurities. The compounds to be separated have similar volatilities as hydroquinone isomers are present and pyrogallol is also present among the impurities to be removed.

The separation of the pyrogallol present in the mixture of the impurities to be removed presented a problem to a person skilled in the art. This is because pyrogallol is a compound which thermally decomposes even more readily than hydroquinone and its decomposition results in colored impurities.

The problem which was posed was that of determining if the hydroquinone could be freed from the colored impurities generated by the thermal decomposition of all or part of the pyrogallol.

There has now been found, and it is this which constitutes the subject matter of the present invention, a process for the purification of a crude hydroquinone $HQ^0$ essentially comprising hydroquinone and small amounts of impurities, including both:

(i) impurities having a lower evaporation temperature than that of hydroquinone, referred to hereinafter as "light impurities", including in particular resorcinol, preferably as major impurity among the light impurities; and (ii) impurities having a higher evaporation temperature than that of hydroquinone, hereinafter denoted by "heavy impurities", including in particular pyrogallol, preferably as major impurity among the heavy impurities, the said process being characterized in that it comprises the following stages:

(A) a topping distillation, in which the crude hydroquinone $HQ^0$ is injected into a distillation column and where the resorcinol is removed as distillation top product, optionally in conjunction with all or part of the other light impurities, whereby a crude mixture M, comprising hydroquinone and the heavy impurities, is recovered at the column bottom; and (B) a tailing distillation, in which the crude mixture M obtained in stage (A) is injected into a distillation column and where the pyrogallol is removed at the column bottom, optionally in conjunction with all or part of the other heavy impurities, whereby hydroquinone in a purified form (HQ) is recovered at the column top.

The inventors have now found that the use of the successive distillation stages (A) and (B) above makes it possible to obtain efficient purification of a crude hydroquinone comprising a mixture of compounds more volatile than hydroquinone and of compounds less volatile than hydroquinone, of resorcinol and pyrogallol type, with the production of a purified hydroquinone with extremely small amounts of residual impurities.

In this context, it should be noted that the process of the invention can be used to treat in particular crude hydroquinones comprising essentially hydroquinone, in a proportion of at least 90% by weight, typically in a proportion of 96 to 99.5% by weight, and of the order of 0.5 to 4% by weight of impurities, for example amounts of impurities as low as from 0.5 to 2% by weight, in order to result, in fine, in purified hydroquinones generally comprising less than 4000 ppm of impurities, most often less than 3000 ppm. More specifically, the process of the invention can in particular be employed in the preparation of hydroquinones of high purity comprising impurities at a content of less than 2500 ppm, typically at most of the order of 2000 ppm, preferably at most of the order of 1500 ppm and more preferably at most of the order of 1000 ppm, indeed even less.

The possibility of such an efficiency in separation proves to be relatively unexpected, insofar as the problem which was posed in terms of separation was particularly difficult to solve, in particular in view of the fact that the various compounds to be separated have very similar relative volatilities. In addition, hydroquinone exhibits a high melting point (172.5° C.) and a very high evaporation point, even under reduced pressure (258° C. under 500 millibar; 208° C. under 100 millibar).

More unexpectedly still, it turns out that, although hydroquinone is sensitive to thermal decomposition and although it is necessary to maintain the hydroquinone at temperatures of 170 to 220° C. throughout the distillation of stages (A) and (B), these stages can nevertheless be efficiently carried out while limiting the phenomena of thermal decomposition of the hydroquinone which are capable of forming colored decomposition products of quinone type.

In this context, the inventors have in particular now demonstrated that stages (A) and (B) can be efficiently carried out while nevertheless limiting the residence time in the distillation columns, whereby the phenomena of thermal decomposition can be very substantially inhibited.

These decomposition phenomena can in addition be still further avoided by limiting the presence of oxygen in the distillation columns, for example while operating under an inert atmosphere.

In addition, the studies of the inventors have made it possible to establish that, under the conditions of the process of the invention, in the case where possible colored products from the thermal decomposition of hydroquinone of quinone type are formed, the latter are substantially recovered at the bottom of the column for the tailing distillation of stage (B).

According to the present invention, it has also been discovered that the pyrogallol and the impurities resulting from its decomposition can be efficiently removed during a distillation operation.

As mentioned above, the pyrogallol at least partially decomposes to give colored impurities owing to the fact that the distillation of the hydroquinone is carried out at high temperature.

It was to be feared that the colored impurities would be re-encountered, in stage (B), in the distillation top product with hydroquinone.

It has been found, according to the invention, that the pyrogallol and the impurities formed by its decomposition remain in the distillation bottom product and can thus be efficiently separated from the hydroquinone.

The invention provides a purification process which makes possible a removal of the various impurities which is both efficient and economic.

On conclusion of stages (A) and (B), the purified hydroquinone is obtained directly in a liquid form.

The exact composition of the crude hydroquinone $HQ^0$ treated according to stages (A) and (B) of the process of the invention can vary to a fairly large extent, the process of the invention proving, however, to be especially advantageous for crude hydroquinones essentially comprising hydroquinone in a proportion of at least 90% by weight and small amounts of impurities of less than 10% by weight. The predominant impurities are resorcinol and pyrogallol, pyrocatechol representing less than 1% of the weight of impurities. The pyrogallol/resorcinol ratio by weight generally varies between 0.2 and 5.

The process of the invention is particularly advantageous in treating crude hydroquinones comprising hydroquinone in a proportion of 96 to 99.5% by weight and contents of impurities of the order of 0.5 to 4% by weight, for example of 0.5 to 2% by weight, in particular of 1 to 2% by weight, with respect to the total weight of the crude hydroquinone.

Typically, a crude hydroquinone $HQ^0$ treated according to the invention comprises from 0.1 to 2% by weight, for example from 0.2 to 1% by weight, of light impurities (having a lower evaporation point than that of hydroquinone), including resorcinol. Resorcinol is generally a major impurity within the light impurities, the light impurities generally comprising at least 50% by weight of resorcinol, with respect to the total weight of the light impurities, for example at least 70% by weight, in particular at least 80% by weight, especially at least 90% by weight, indeed even more. In addition to resorcinol, the light impurities present in the crude hydroquinone $HQ^0$ can in particular comprise pyrocatechol.

Furthermore, in the crude hydroquinone $HQ^0$, the amount of heavy impurities (having a greater evaporation point than that of hydroquinone) is usually from 0.1 to 2% by weight, for example from 0.2 to 1% by weight. These heavy impurities include in particular pyrogallol, generally as major heavy impurity, in general in combination with other heavy impurities, in particular tars or also thermal decomposition products of hydroquinone, such as quinones. Thus, the heavy impurities generally comprise at least 50% by weight of pyrogallol, with respect to the total weight of the heavy impurities, for example at least 70% by weight, indeed even at least 80% by weight, in particular at least 90% by weight, or more.

According to a specific embodiment, the crude hydroquinone $HQ^0$ treated according to stages (A) and (B) is obtained or is capable of being obtained from a reaction mixture resulting from the hydroxylation of phenol by hydrogen peroxide in the presence of acid catalysts of the type mentioned above in the present description, after substantial removal of the pyrocatechol by distillation.

A crude hydroquinone $HQ^0$ suited to the process of the invention comprises, by weight with respect to the total amount of crude hydroquinone:
  from 96 to 99.5% of hydroquinone,
  from 0.1 to 2%, preferably from 0.2 to 1%, of resorcinol,
  from 0.1 to 2%, preferably from 0.2 to 1%, of pyrogallol,
  optionally pyrocatechol in the form of traces, typically at a
    content of less than 500 ppm (0.05%), preferably of less than 100 ppm (0.01%).

Whatever the exact nature of the crude hydroquinone $HQ^0$ treated according to the process of the invention, the distillation stages (A) and (B) are advantageously carried out under the conditions set out below.

The topping distillation stage (A) is targeted at removing the resorcinol and preferably substantially all the light impurities present in the crude hydroquinone $HQ^0$ by entraining them at the column top, in order to recover, at the column bottom, a crude mixture M essentially comprising hydroquinone and heavy impurities which is depleted in light impurities, in particular in resorcinol.

It should be noted that the removal of the impurities at the column top is generally accompanied by the departure of a fraction of hydroquinone at the column top, which is thus not recovered in the crude mixture M which will be employed in stage (B). In order to limit this loss of hydroquinone in stage (A), it is possible in particular to vary the number of theoretical stages and the reflux ratio of the distillation column used in stage (A), whereby it is typically possible to obtain, in the process, a (lost hydroquinone/hydroquinone in the mixture M) ratio of less than 2%, for example of between 0.2 and 1%, in particular between 0.3 and 0.7%.

The feed flow rate of the crude hydroquinone $HQ^0$ in the distillation column of stage (A) can vary to a fairly large extent, in particular according to the proportions chosen for the column and the flow rate desired in fine for the purified hydroquinone. Without implied limitation, it may simply be specified that it is possible to operate with feed flow rates ranging up to 3000 kg/h, indeed up to 5000 kg/h. Typically, it is possible to employ flow rates of the order of 100 to 3000 kg/h.

In stage (A), the feed point where the crude hydroquinone $HQ^0$ is introduced is generally substantially at mid-height in the distillation column, namely with a ratio by volume of the rectification region of the column of stage (A) to the stripping region of the column of stage (A) generally of between 25:75 and 75:25, more preferably between 30:70 and 70:30, for example between 40:60 and 60:40. The term "rectification region" is understood here to mean the internal volume of the distillation column of stage (A) which is situated above the horizontal plane comprising the feed point, in contrast to the "stripping region", corresponding to the internal column volume situated below this horizontal plane.

The stream which exits at the top of the distillation column of stage (A), which essentially comprises the light impurities to be removed and a small amount of hydroquinone, can advantageously be partially diverted, in order to be reinjected into the distillation column, according to the reflux technique. The amount of stream which is reinjected into the column can be quantified by a reflux ratio, defined by the ratio of the flow rate effectively exiting at the outlet of the column top to the flow rate of material reinjected from the top of the column towards the interior of the column. In the column of the topping distillation of stage (A), this reflux ratio is advantageously between 300 and 2000, typically between 400 and 1500, for example between 500 and 1000.

Furthermore, the number of theoretical stages of the column used in stage (A) is advantageously at least 20, preferably at least 30, for example between 30 and 50.

Moreover, the residence time of the hydroquinone in the column of stage (A) is preferably less than 1 hour, preferably less than 45 minutes and more preferably still less than 30 minutes, which makes it possible in particular in inhibit the phenomena of thermal decomposition of hydroquinone by limiting the time during which the latter is subjected to high temperature. Nevertheless, this residence time generally remains at least equal to 10 minutes, for example at least 15 minutes, in particular in order to make possible efficient separation of the light impurities in stage (A). A good compromise between separation and inhibition of thermal decomposition is thus obtained in stage (A) with residence times typically of the order of 15 to 30 minutes.

Stage (B), which follows stage (A), for its part consists of a tailing distillation which is targeted at removing the pyrogallol present in the crude mixture M obtained on conclusion of the topping distillation and preferably substantially all the heavy impurities. In stage (B), contrary to stage (A), it is the impurities which are sent into the column bottom and it is at the column top that hydroquinone is recovered in the purified form.

Here again, the removal of the impurities towards the column bottom is accompanied by the departure of a portion of the hydroquinone at the column bottom. Thus, not all the hydroquinone in the mixture M is recovered at the column top. In order to limit this loss of hydroquinone at the distillation column bottom of stage (B), it is possible in particular to vary the reflux ratio and the number of theoretical stages of the distillation column of stage (B), whereby it is possible typically to obtain, in stage (B), a (lost hydroquinone/hydroquinone recovered in the purified hydroquinone) ratio of less than 2%, for example of between 0.2 and 1%.

In stage (B), the feed point where the crude mixture M resulting from the column bottom of stage (A) is introduced is in general substantially at mid-height in the distillation column. Typically, for the column of stage (B), the ratio by volume of the rectification region to the stripping region is between 25:75 and 75:25, more preferably between 30:70 and 70:30, for example between 40:60 and 60:40. Here again, the term "rectification region" is understood to mean the internal volume of the distillation column of stage (B) which is situated above the horizontal plane comprising the feed point, in contrast to the "stripping region", corresponding to the internal volume of the column situated below this horizontal plane.

Furthermore, as in stage (A), the operation is advantageously carried out at reflux in stage (B), namely by diverting a portion of the stream which exits at the top of the distillation column of stage (B), which comprises purified hydroquinone, in order to reinject the stream into the distillation column. The reflux ratio in the column of the tailing distillation of stage (B), defined by the ratio of the flow rate effectively exiting at the outlet of the column top to the flow rate of material reinjected from the top of the column into the column is advantageously between 1 and 15, typically between 3 and 12, for example between 4 and 10.

Furthermore, the number of theoretical stages of the column used in stage (B) is advantageously at least equal to 20, preferably at least equal to 30, for example between 30 and 50.

In stage (B), it is very particularly important to control the residence time of the hydroquinone in the distillation column.

Moreover, in order to prevent thermal decomposition of the product, it is generally advantageous to choose a residence time of less than 1 hour, more advantageously of less than 30 minutes, in the column of stage (B). In order to obtain efficient separation of heavy impurities in stage (B), it is, however, generally preferable to operate with residence times of the hydroquinone in the column of stage (B) of at least 10 minutes, for example between 15 and 30 minutes.

More generally, it should be noted that stages (A) and (B) are carried out under conditions which make possible the distillation of the hydroquinone, which implies in particular that they are carried out at temperatures sufficient for the hydroquinone to exist in the liquid or gaseous state. It is indicated to avoid the presence of any cold spot below 170° C. (solidification temperature of hydroquinone) in the device in which the distillation stages (A) and (B) are carried out, which might cause phenomena of fouling of the columns harmful to the output and/or to the quality of the distillation, indeed even phenomena in which the product sets solid, which would necessitate a complete shutdown of the process and expensive operations for cleaning the plant. To this end, to be safe, it is generally preferable for all the internal regions of the distillation columns employed for stages (A) and (B) to be at least at a temperature of 175° C. and preferably at a temperature of at least 180° C., for example of at least 185° C. The majority of the regions are greater than these temperatures, in order to achieve the evaporation of the hydroquinone necessary for the distillation, the temperature nevertheless typically remaining below 220° C.

As a general rule, in order to obtain the high temperatures required, without the presence of cold spots, use is advantageously made of jacketed columns while circulating a heat-exchange fluid brought to a temperature of the order of 180 to 220° C. Mention may in particular be made, as appropriate heat-exchange fluids, of heavy esters of carboxylic acids, such as octyl phthalate, aromatic ethers, such as diphenyl ether and/or benzyl ether, biphenyl, terphenyls, other polyphenyls which are optionally partially hydrogenated, paraffinic and/or naphthenic oils, or also some oil distillation residues.

Furthermore, it is desirable to avoid as much as possible the establishment of heat bridges between the device employed according to the invention and the external environment, in order to guard against any risk of heat losses.

Furthermore, in view of the high temperatures used, it is generally desirable to avoid the presence of oxygen in the distillation stages of stages (A) and (B), in particular in order to avoid any decomposition of the hydroquinone to quinones. To this end, these stages are advantageously carried out under an inert atmosphere substantially devoid of oxygen, for example under nitrogen or else under argon, nitrogen being preferred, in particular in view of its low cost.

Moreover, in particular in order to avoid having to heat to excessively high temperatures, the distillations of each of stages (A) and (B) are advantageously carried out under reduced pressure; these pressures, which are identical or different in the distillation columns of stages (A) and (B), are typically between 50 and 100 millibar, for example between 60 and 90 millibar. The operating pressures of stages (A) and (B) can be identical or different.

The distillation of stages (A) and (B) can advantageously be carried out according to a continuous mode, in particular by injecting the crude hydroquinone $HQ^0$ to be treated at a constant flow rate at the inlet of the topping distillation column. However, it is not out of the question to carry it out according to the batchwise mode.

Whatever their exact embodiment, stages (A) and (B) result, in fine, at the top of the column of stage (B), in a purified hydroquinone HQ, obtained after condensation in the liquid state, which does not pose the handling problems encountered with hydroquinone powders.

The purified hydroquinone HQ obtained in the liquid state on conclusion of stages (A) and (B) is generally cooled, preferably under an atmosphere of inert gas which is substantially devoid of oxygen (nitrogen or argon, for example) in order to avoid any decomposition of hydroquinone, and formed in the form of solid objects having a size suitable for handling without risks of dust formation, typically of the order of at least a few hundred microns to a few millimeters.

This forming can in particular be carried out by employing one or other of the following techniques:

- a flaking on a cylinder or on a belt, in which the liquid hydroquinone is brought into contact with a colder metal cylinder or belt and then the film obtained on the cylinder is scraped off with a blade, whereby the solid hydroquinone is recovered in the form of flakes,
- a prilling, such as described in particular in EP-A 1 556 322, in which the liquid hydroquinone is dispersed in the form of drops in a current of air, for example by dropping it from the top of a tower into a column of cold air, which results in the solid hydroquinone being obtained in the form of beads,
- a quenching, where the liquid hydroquinone is dispersed, generally in the form of drops, in a cold immiscible liquid, whereby solid hydroquinone is obtained in the form of granules.

Whatever its final form, the purified hydroquinone obtained according to the process of the invention comprises a very low level of impurities, generally less than 4000 ppm of impurities, generally less than 3000 ppm.

According to a specific embodiment, the process of the invention can be employed in the preparation of hydroquinone of high purity, typically comprising less than 2500 ppm of impurities, preferentially less than 2000 ppm of impurities. Such a hydroquinone of high purity advantageously comprises less than 2000 ppm of light impurities, such as resorcinol or pyrocatechol (traces), this content of light impurities preferably being less than 1500 ppm, for example between 1000 and 1500 ppm and more preferably between 300 and 1000 ppm. The content of heavy impurities is, for its part, advantageously less than 500 ppm, preferably less than 300 ppm, for example between 20 and 200 ppm.

The process of the invention makes it possible to effectively remove the impurities since the contents of resorcinol and of pyrogallol may respectively fall as far as to 300 ppm and 20 ppm and pyrocatechol can no longer be detected by the analysis.

The solid hydroquinones as obtained according to the invention furthermore exhibit a very low content of thermal decomposition products, such as quinones, in particular when the process is carried out while avoiding any contact of the heated hydroquinone with oxygen. This low content of decomposition products is reflected by a substantial absence of coloring of the purified hydroquinone obtained, which has a white appearance. The coloring of the hydroquinone can be measured more precisely by colorimetric analysis of an aqueous solution of said hydroquinone, typically by producing a 5% by weight solution at ambient temperature. It is possible to obtain low colorimetric indices of, for example, between 20 and 200 Hazen and more preferably between 20 and 100 Hazen for the purified hydroquinones of the invention.

According to another more specific aspect, another subject matter of the present invention is a device for the implementation of the process of the invention.

This device, which is generally provided in the form of a plant of industrial dimensions, comprises:
- a first distillation column suited to the topping distillation of a crude hydroquinone $HQ^0$ according to the above-mentioned stage (A), designed in order to remove the resorcinol at the column top and to recover, at the column bottom, a mixture comprising most of the hydroquinone and the heavy impurities; and
- a second distillation column suited to the tailing distillation of the abovementioned stage (B), the inlet of which is connected to the column bottom of the first column, designed in order to remove, at the column bottom, the pyrogallol present in the crude mixture originating from the column bottom of the first distillation column and in order to obtain, at the column top, the hydroquinone in purified form.

In this device, the two distillation columns advantageously exhibit the preferential characteristics as defined above in the present description. In particular, the columns are preferably jacketed columns heated by a heat-exchange fluid of the above-mentioned type.

The invention will be clarified still more by means of the description which follows, made with reference to the appended figures, where:

Figure 1:
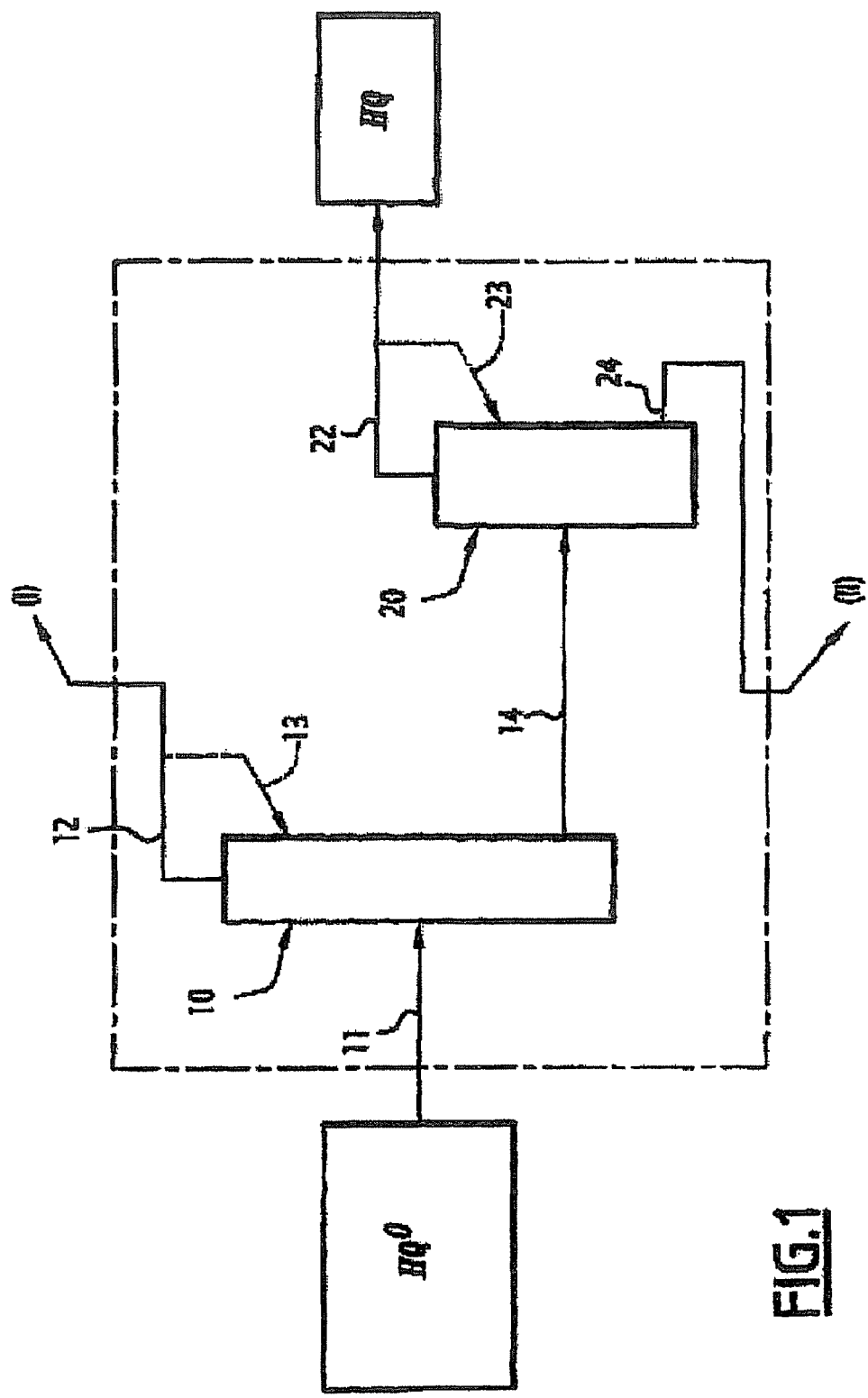
FIG. 1 is a diagrammatic representation of the general device used according to the invention for the implementation of the distillation stages (A) and (B).

In FIG. 1, which illustrates the general principle of the process of the invention, crude hydroquinone $HQ^0$ (11), which is a mixture of hydroquinone, of light impurities comprising resorcinol and of heavy impurities comprising pyrogallol, is introduced into a first distillation column (10): the feeding of the column (10) is preferably located substantially at mid-height in the column.

The topping distillation [stage (A)] which is carried out in the column (10) results, in the column (10) top, in the removal of a stream, symbolized by (I) in FIG. 1, comprising resorcinol and optionally other light impurities, and also a fraction of the hydroquinone. This stream (I) coming from the column top can subsequently be treated, recycled or removed, in particular by a treatment in a burner. The stream (12) which exits at the column (10) top is partially diverted (13) in order to be reinjected into the column (10), generally laterally at the column top, in order to provide for reflux in the column, which reflux is installed in particular in order to improve the efficiency of the separation.

At the same time, in the column (10) bottom, a crude mixture M (14) is obtained which comprises hydroquinone and heavy impurities, with possibly traces of light impurities not extracted during the preceding stage. This crude mixture M is introduced into a second distillation column (20), the feeding of the column (20) preferably being substantially at mid-height. The crude mixture M resulting from the column (10) will be subjected, in this column (20), to the tailing distillation of stage (B).

In the column (20), the distillation results in the separation, on the one hand, of a purified hydroquinone HQ (22), recovered at the column (20) top and obtained after condensation in the liquid form, and, on the other hand, of a stream (24), symbolized by (II) in FIG. 1, comprising pyrogallol and optionally other heavy impurities (and also a small amount of hydroquinone) which are discharged at the column (20) bottom. This stream (II) which exits at the column (20) bottom is subsequently treated, removed or recycled. Here again, it is advantageous to install reflux (23) by diverting a portion of the stream (22), in particular in order to improve the efficiency of the separation of the heavy impurities.

A purified hydroquinone (22), which essentially no longer comprises impurities and which has been liquefied after passing into a condenser, is obtained at the top of the column (20). This liquid hydroquinone is subsequently cooled and formed, for example by flaking on a cylinder or on a belt (this stage not being represented in the figure).

Figure 2:
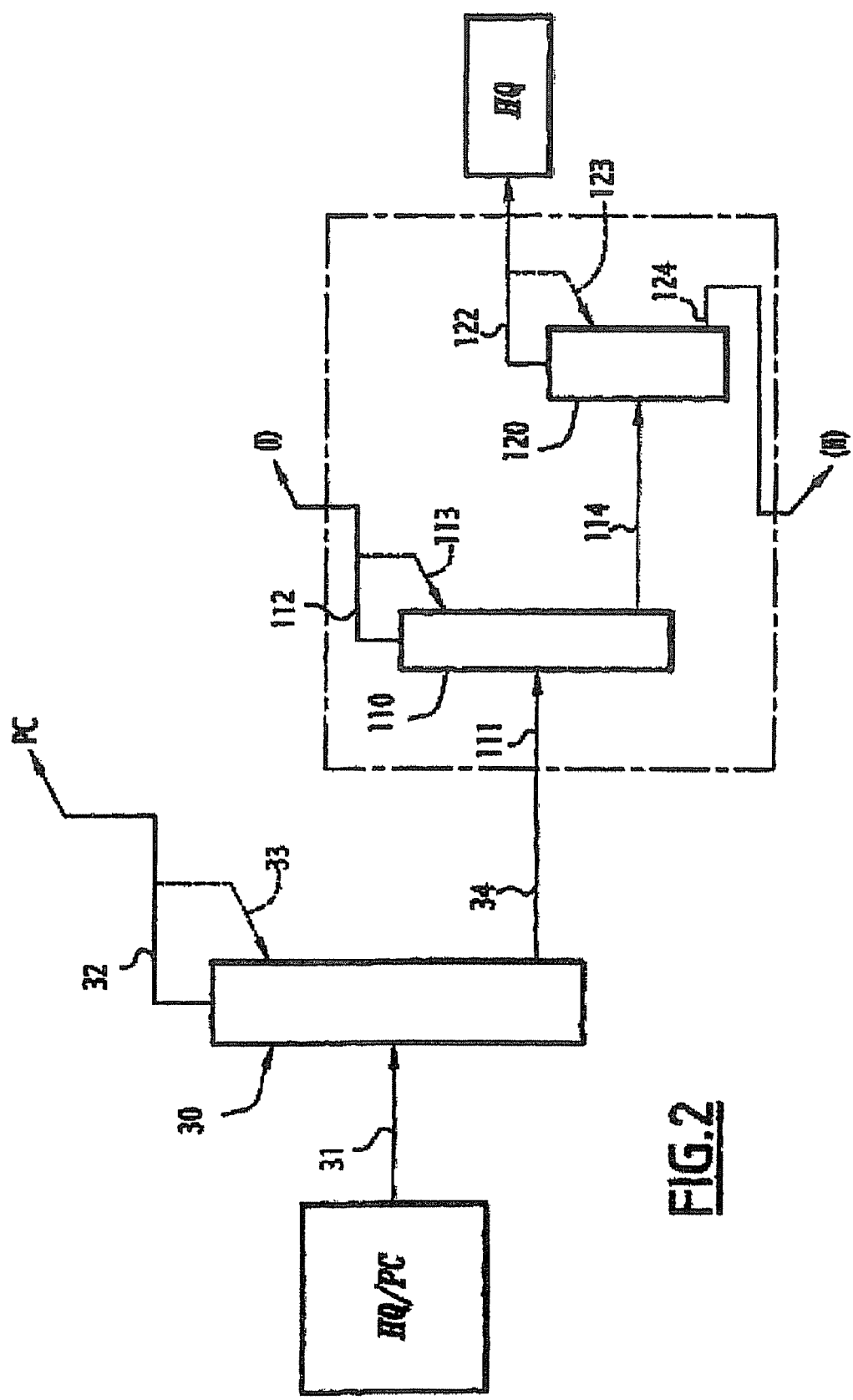
FIG. 2 is a diagrammatic representation of a device employing a specific alternative form of the invention, according to which purified hydroquinone is prepared starting from a mixture such as results from a reaction for the hydroxylation of phenol by hydrogen peroxide in the presence of a catalyst of strong protic acid type.

In FIG. 2, a device of the abovementioned type is employed in a more complex process for the treatment of an HQ/PC mixture of the type obtained on conclusion of a hydroxylation of phenol by hydrogen peroxide in the presence of a catalyst, this HQ/PC mixture essentially comprising pyrocatechol (PC) and hydroquinone and small amounts of light impurities (resorcinol) and heavy impurities (pyrogallol).

This HQ/PC mixture (31) feeds a first distillation column (30) intended to substantially remove the pyrocatechol (32) at the column top. Here again, it is advantageous to install reflux (33) by diverting a portion of the stream (32). A purified pyrocatechol (32) is obtained at the column (30) top.

Whatever the embodiment of the distillation in the column (30), a crude hydroquinone $HQ^0$ (34), essentially comprising hydroquinone (typically between 96 and 99.5%) in combination with small amounts of impurities, namely of the order of 0.1 to 2% of light impurities (resorcinol and traces of pyrocatechol) and of the order of 0.1 to 2% of heavy impurities (essentially pyrogallol), is obtained at the column (30) bottom.

This crude hydroquinone $HQ^0$ is subsequently subjected to a topping distillation treatment in the column (110), where the light impurities (resorcinol and traces of pyrocatechol) are removed at the column (110) top in the form of a stream symbolized by (I) in FIG. 2. The stream which exits at the column top (112) is partially diverted (113) in order to be reinjected into the column (110) in order to provide reflux. A crude mixture (114), comprising hydroquinone and the heavy impurities (essentially pyrogallol), is recovered at the column (110) bottom.

The crude mixture thus obtained is introduced into the column (120), preferably substantially at mid-height. It is subjected, in this column, to a tailing distillation, resulting in the recovery, at the column (120) top, of purified hydroquinone HQ (122), advantageously provided with reflux (123). For their part, the heavy impurities are removed at the column (120) bottom in the form of a stream (124) symbolized by (II) in FIG. 2.

Thus, the process illustrated in FIG. 2 makes possible the efficient separation, in the isolated and purified (thus enhanced in value) form, of the two main constituents (pyrocatechol and hydroquinone) present in the reaction media resulting from a reaction for the hydroxylation of phenol by hydrogen peroxide in the presence of an acid catalyst. This process can in addition be carried out continuously. This particular embodiment of the process constitutes a specific subject matter of the present invention.

The invention will be still further illustrated by the example below, which describes, without implied limitation, a possible embodiment of the invention.

EXAMPLE

A device as represented in FIG. 1, employed continuously, was used to purify a crude hydroquinone comprising, by weight with respect to the total weight of the crude hydroquinone, 0.6% of resorcinol and 0.7% of pyrogallol.

This mixture was introduced into the first distillation column (10) with a constant feed flow rate of 100 kg/h.

The column (10) used exhibits the following characteristics:

| | |
|---|---|
| number of theoretical stages: | 30 |
| column top temperature: | 202° C. |
| working pressure: | 87 mbar |
| reflux ratio: | 600 |

The residence time of the hydroquinone in the column (10) is evaluated at 25 min.

A stream (I) comprising resorcinol was obtained at the top of the column (10), the resorcinol having a flow rate of 1 kg/h.

The second column (20), into which the crude mixture obtained at the bottom of the first column (10) was introduced, was for its part used under the following conditions:

| | |
|---|---|
| number of theoretical stages: | 30 |
| column top temperature: | 201° C. |
| working pressure: | 73 mbar |
| reflux ratio: | 7 |

The residence time of the hydroquinone in the column (20) is evaluated at 30 min.

The stream (24) comprising the pyrogallol at the bottom of the column (20) has a flow rate of 1 kg/h.

A purified hydroquinone HQ was obtained at the top of the column (20), which hydroquinone exits with a flow rate of 98 kg/h.

This hydroquinone comprises less than 2000 ppm of resorcinol and less than 200 ppm of pyrogallol.

It thus has a purity of 99.78% by weight.

The hydroquinone obtained exhibits a coloring of 30 Hazen.

What is claimed is:

1. A process for the purification of a crude hydroquinone $HQ^0$ comprising hydroquinone and amounts of impurities, including both:
    (i) impurities having a lower evaporation temperature than that of hydroquinone, referred to as light impurities, including resorcinol; and
    (ii) impurities having a higher evaporation temperature than that of hydroquinone, referred to as heavy impurities, including pyrogallol,
    the process which consists essentially of the following stages:
(A) a topping distillation, comprising introducing the crude hydroquinone $HQ^0$ into a topping distillation column and removing the resorcinol as distillation top product, optionally in conjunction with all or part of the light impurities, recovering a crude mixture M, comprising hydroquinone and the heavy impurities, at the topping column bottom, wherein a reflux ratio in the topping distillation column is between 300 to 2,000; and
(B) a tailing distillation, comprising injecting the crude mixture M obtained in stage (A) into a tailing distillation column and removing the pyrogallol at the column bottom, optionally in conjunction with all or part of the heavy impurities, recovering hydroquinone in a purified form (HQ) at the tailing column top.

2. The process as defined by claim 1, wherein the crude hydroquinone $HQ^0$ comprises from 96% to 99.5% by weight of hydroquinone and from 0.5% to 4% by weight of impurities.

3. The process as defined by claim 1, wherein the crude hydroquinone $HQ^0$ comprises from 0.1% to 2% by weight of light impurities.

4. The process as defined by claim 1, wherein the crude hydroquinone $HQ^0$ comprises from 0.1% to 2% by weight of heavy impurities.

5. The process as defined by claim 1, wherein the light impurities present in the crude hydroquinone $HQ^0$ comprise at least 50% of resorcinol with respect to the total weight of the light impurities.

6. The process as defined by claim 1, wherein the heavy impurities present in the crude hydroquinone $HQ^0$ comprise at least 50% of pyrogallol with respect to the total weight of the heavy impurities.

7. The process as defined by claim 1, wherein the crude hydroquinone $HQ^0$ is obtained from a reaction mixture resulting from a hydroxylation of phenol by hydrogen peroxide in the presence of acid catalysts, after substantial removal of the pyrocatechol by distillation.

8. The process as defined by claim 1, wherein the crude hydroquinone $HQ^0$ comprises, by weight with respect to the total amounts of crude hydroquinone:
    from 96% to 99.5% of hydroquinone,
    from 0.1% to 2% of resorcinol,
    from 0.1% to 2% of pyrogallol, and
    optionally, trace amount of pyrocatechol.

9. The process as defined by claim 1, wherein in stage (A), the feed point where the crude hydroquinone $HQ^0$ is introduced is substantially at mid-height in the distillation column, with a ratio by volume of a rectification region of the column of stage (A) to a stripping region of the column of stage (A) of from 25:75 to 75:25.

10. The process as defined by claim 1, wherein the number of theoretical stages of the column in stage (A) is at least 20.

11. The process as defined by claim 1, wherein the residence time of the hydroquinone in the column of stage (A) ranges from 10 minutes to 1 hour.

12. The process defined by claim 1, wherein in stage (B), the feed point where the crude mixture M is introduced is substantially at mid-height in the distillation column, with a ratio by volume of the rectification region of the column of stage (B) to a stripping region of the column of stage (B) of from 25:75 to 75:25.

13. The process as defined by claim 1, wherein the stream which exits at the top of the distillation column of stage (B) is partially diverted, and reinjected into the distillation column, with a reflux ratio of from 1 and 15.

14. The process as defined by claim 1, wherein the number of theoretical stages of the column in stage (B) is at least 20.

15. The process as defined by claim 1, wherein the residence time of the hydroquinone in the column of stage (B) ranges from 10 minutes to 1 hour.

16. The process as defined by claim 1, wherein stages (A) and (B) are carried out under an inert atmosphere substantially devoid of oxygen.

17. The process as defined by claim 1, wherein stages (A) and (B) are carried out at pressures of from 50 to 100 millibar.

18. The process as defined by claim 1, wherein the purified hydroquinone HQ obtained in liquid state on conclusion of stages (A) and (B) is cooled and formed in the form of solid objects having a size of at least a few hundred microns to a few millimeters.

19. A device for conducting the process as defined by claim 1, which comprises:

a first distillation column (10; 110) provided for the topping distillation of a crude hydroquinone $HQ^0$ according to stage (A), designed to obtain, at the column top, the light impurities (12; 112) and to recover, at the column bottom, a mixture (14; 114) comprising most of the hydroquinone and the heavy impurities; and a second distillation column (20; 120) suited to the tailing distillation of the stage (B), the inlet of which is connected to the column bottom of the first column (10; 110), designed to remove, at the column bottom, the heavy impurities (24; 124) present in the mixture (14; 114) originating from the column bottom of the first distillation column and to obtain, at the column top, the hydroquinone in purified form (22; 122).

20. The process as defined by claim 1, wherein the purified hydroquinone (HQ) comprises less than 4,000 ppm of impurities.

* * * * *